Jan. 8, 1963 C. FISCHER Plant Pat. 2,216
GLADIOLUS PLANT
Filed March 27, 1962
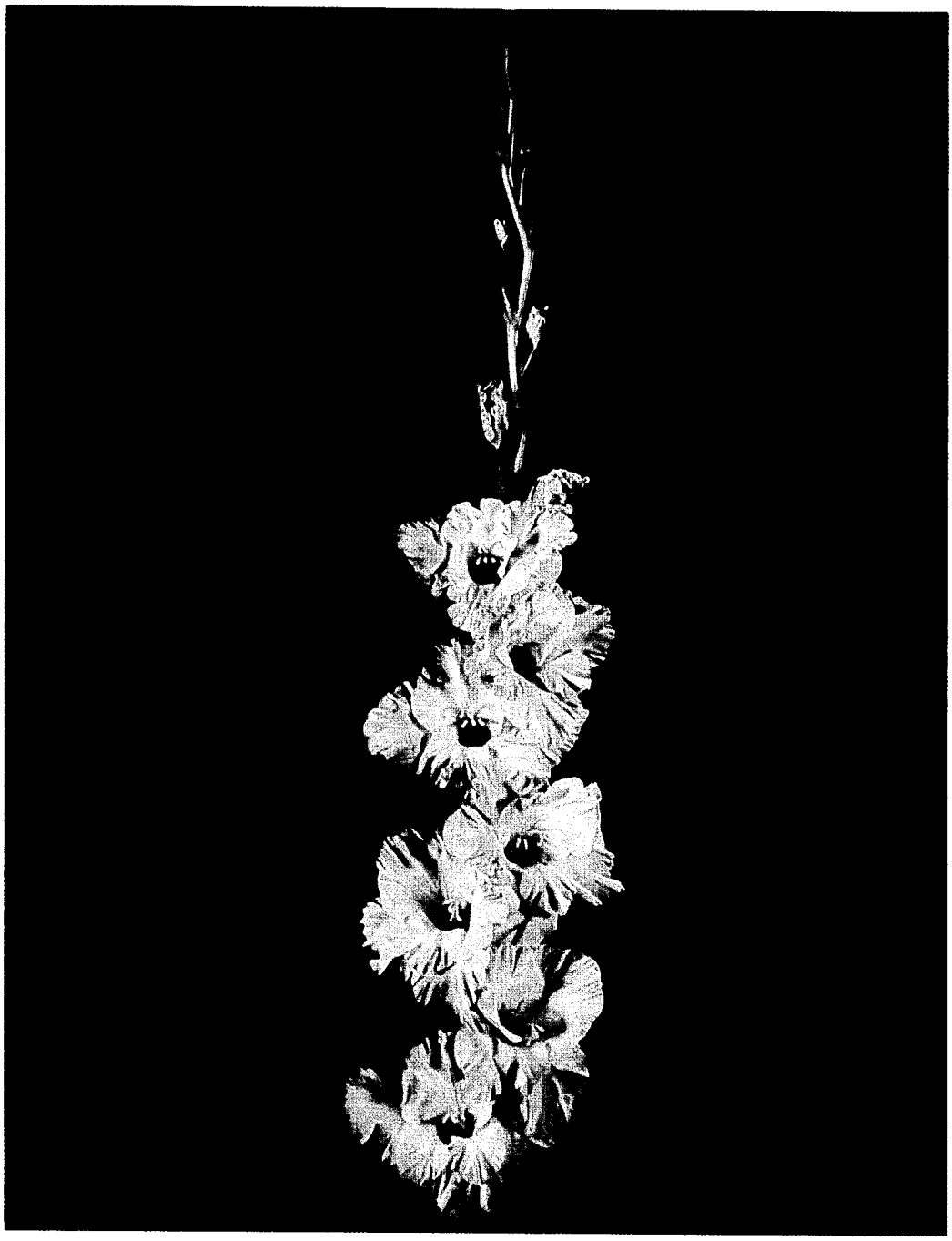
Inventor.
Carl Fischer
By: Robb & Robb
Attorneys.

United States Patent Office

Plant Pat. 2,216
Patented Jan. 8, 1963

2,216
GLADIOLUS PLANT

Carl Fischer, St. Charles, Minn., assignor to Imperial Flowers Limited, Leamington, Ontario, Canada, a corporation of Canada Filed Mar. 27, 1962, Ser. No. 182,985
1 Claim. (Cl. 47—60)

The present invention relates to a new and distinct variety of gladiolus plant which was originated by me by crossing the variety "Prospector" (unpatented) with an unnamed and unpatented seedling of unidentified origin, the former of which was the seed parent, and the latter the pollen parent.

The primary objective of this breeding was to produce a new gladiolus variety having rugged and early blooming habits and which bears pink flowers. This objective was fully achieved, in combination with other improved and desirable features, as evidenced by the following unique combination of characteristics which are outstanding in the new variety and which distinguish it from its parents, as well as from all other varieties of which I am aware:

(1) A rugged and vigorous habit of growth;
(2) An early blooming habit;
(3) An intensely ruffled form of the flower petals; and
(4) A distinctive and attractive general color tonality of the flowers corresponding to Empire Rose over the major area, shading to a slightly darker Empire Rose color at the edges, said flowers having a yellow throat defined principally on the three lower petals, with the yellow color extending over a small area of the two outer petals, with a shading of Mallow Purple on the reverse of the petals at the base where the floret is attached to the calyx.

My new variety resembles the variety known as "Heroine" (unpatented) more than any other known variety, but differs therefrom particularly by a heavier flower substance, a more heavy ruffling of the flowers, and a larger and deeper yellow flower throat.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely vigorous; excellent propagator; blossom spike attains height of about 58 inches to 60 inches.

Blooming habit: Extremely early in the northern latitudes of the United States; comes into bloom from the planting of large bulbs in about 65 to 70 days.

Stems: Straight and willowy.
*Diameter at base.*—About ⅜ inch.
*Color (at base).*—Roseine Purple, Plate 624/1.

Foliage: Upright; slender; leaves range from 1¼ inches to 1½ inches wide; leaves attain height of about 36 inches. Color—healthy green.

Disease resistance: Unusually resistant to Fusarium yellows, Sclerotinia dry rot and Septoria leaf spot, as determined by comparison with other varieties grown in my fields near St. Charles, Minnesota, in irrigated black loam soil.

Corms (bulbs): Round; plump; healthy; well-husked. Color of flesh—Chinese Yellow, Plate 606/2.

*Flower*

Spike: Medium length; flower head ranges from about 24 inches to 26 inches long; bears from 14 to 16 buds, with 6 or 7 usually open at one time and with 5 or 6 buds showing color.

Bud:
*Size.*—About 2½ inches long when opening.
*Opening.*—5 or 6 buds show color at one time.

Flower:
*Arrangement.*—Florets are informally or alternately arranged on stems and usually all facing forward.
*Size.*—Individual florets average about 5 inches in diameter, with upper blooms being progressively smaller.
*Form.*—Round, flat florets, with petals heavily ruffled.
*Keeping qualities.*—Need to be cut in loose bud stage in order to open well.

Petals:
*Shape.*—Round; creased; intensely ruffled.
*Size.*—Outer petals—2¼ inches wide. Lip petal—1¼ inches wide.
*Aspect.* — Extremely heavy substance; generally smooth surface, with some creasing; intensely ruffled.
*Fragrance.*—None.
*Color.*—Empire Rose, Plate 0621/2 over major area, shading to Empire Rose, Plate 0621/1 at edges, giving general color effect as Empire Rose, Plate 0621/2; three lower petals have Naples Yellow, Plate 403 on areas defining flower throat, with the yellow color confined to a small area of the two outer petals; shading of Mallow Purple, Plate 630/1 on reverse of petals at the base where the floret is attached to calyx.

*Reproductive Organs*

Stamens: Color—Spectrum Violet, Plate 635/3.
Pistil: Color—Spinel Pink, Plate 0625/1.

I claim:

A new and distinct variety of gladiolus plant, substantially as herein shown and described, characterized particularly as to novelty by the unique combination of a rugged and vigorous habit of growth, an early blooming habit, intense ruffling of the flower petals, and a distinctive and attractive general color tonality of the flowers corresponding to Empire Rose, said flowers having a yellow throat and having a shading of Mallow Purple on the reverse of the petals at the base where the florets are attached to the calyx.

No references cited.